United States Patent [19]

Hirdes

[11] Patent Number: 4,768,955
[45] Date of Patent: Sep. 6, 1988

[54] DENTAL APPLIANCE FOR INTRODUCING A FILLER MATERIAL INTO A TOOTH CAVITY

[76] Inventor: Rüdiger Hirdes, Kleinherbeder Str. 9a, 5810 Witten, Fed. Rep. of Germany

[21] Appl. No.: 906,918

[22] Filed: Sep. 11, 1986

[30] Foreign Application Priority Data

Sep. 19, 1985 [DE] Fed. Rep. of Germany ....... 3533367

[51] Int. Cl.$^4$ .............................................. A61C 5/04
[52] U.S. Cl. .......................................... 433/89; 433/90
[58] Field of Search ........................ 433/89, 90, 81, 82, 433/83, 87

[56] References Cited

U.S. PATENT DOCUMENTS

| | | | |
|---|---|---|---|
| 3,028,672 | 10/1959 | Zandberg | 433/90 |
| 3,221,409 | 12/1965 | Thiel et al. | 433/83 |
| 3,638,314 | 2/1972 | Lopez | 433/90 |
| 3,751,807 | 8/1973 | Noll et al. | 433/89 |
| 3,792,530 | 2/1974 | Smith | 433/83 |
| 3,990,152 | 11/1976 | Hirdes | 433/89 |
| 4,092,778 | 6/1978 | Hirdes | 433/83 |
| 4,306,863 | 12/1981 | Law | 433/83 |
| 4,340,367 | 7/1982 | Vadas et al. | 433/89 |
| 4,377,380 | 3/1983 | Vadas et al. | 433/89 |

FOREIGN PATENT DOCUMENTS

2364547 of 0000 Fed. Rep. of Germany ........ 433/83

Primary Examiner—John J. Wilson
Assistant Examiner—Michael Lynch
Attorney, Agent, or Firm—Michael J. Striker

[57] ABSTRACT

A dental appliance for introducing a filler material into a tooth cavity, comprises a support, a filler pipe, units forming a first passage, a filler expelling element reciprocatingly movable in the first passage, the filler expelling element merging into the filler pipe and having a front end, a removable magazine which accommodates a filler a plurality of parts of which can be expelled therefrom, the magazine extending transversely to the filler pipe and opening into the latter, the magazine having an inlet opening which opens into the filler pipe and is provided with an upper edge, a second passage, a magazine expelling element guided in the second passage for pressing a portion of the filler from the magazine into the filler pipe, the filler expelling element and the magazine expelling element being surrounded by the support, and a mechanical transmission unit which couple the filler expelling element and the magazine expelling element with one another to provide coordination of their movements, the transmission unit including a toothed rack which is connected with the magazine expelling element, an expelling lever which is turnably connected with the support and having a free end engaging in the toothed rack and expelling button which is actuatable by a finger and connected with the filler expelling element, and a projection, the lever being arranged so that during the working stroke it displaces with the toothed rack via the expelling button and the projection in direction toward the filler pipe before the front end of the filler expelling element reaches the upper end of the opening of the magazine into the filler pipe.

16 Claims, 5 Drawing Sheets

DENTAL APPLIANCE FOR INTRODUCING A FILLER MATERIAL INTO A TOOTH CAVITY

BACKGROUND OF THE INVENTION

The present invention relates to a dental appliance for introducing a filler material into tooth cavities.

More particularly, it relates to a dental appliance which has a filler pipe, a filler expelling element which is reciprocable in a first passage and merges into the filler pipe, a replaceable magazine which extends transversely to the filler pipe and opens into the latter, so that a part of the filler material such as amalgam is pressed from the magazine via a second passage by a magazine expelling element in a working stroke which starts above the opening of the magazine and ends at the outlet of the filler pipe, so as to press the part of the filler material into the filler pipe. A mechanical transmission couples the filler expelling element and the magazine expelling element surrounded by a common housing so as to coordinate their movements. A toothed rack is connected with the magazine expelling element and forms a part of the above mechanical transmission.

A known dental appliance of this type is disclosed, for example, in the German Patent No. 2,364,547. It is characterized by a mechanical transmission which is driveable from a power source, on the one hand, and by a pneumatic drive which is set into operation from a pressure air source. In addition to the complicated construction, the above mentioned dental appliance is dependent from an energy source which is connectable with it via a connecting conduit. The connecting conduit considerably affects the ergonomy and manipulation of the appliance, and on the other hand the requirement of an energy source limits the operational region of such an appliance in a medical practice. Finally, after emptying of the magazine, a new magazine must be inserted promptly, or treatment must continue with a second appliance.

U.S. Pat. No. 3,792,530 discloses a further appliance of a different type in which a filler expelling element is guided with a play in a guiding passage by means of a piston arranged at its front end, and a magazine expelling element is guided in a second guiding passage by a further piston. The filler expelling element and the magazine expelling element are acted upon at their rear ends by the force of springs. These springs have the purpose of holding the piston of the filler expelling element in a withdrawn position from the filler pipe inside an inner space of an opening, until the slider engaging the rear end of the filler expelling element is manually moved forwardly. The spring has the purpose of pressing the filler material from the second guiding passage which serves as a reserve container, into the upper hollow space of the filler pipe. The rear end of the magazine expelling element is provided with a toothed rack which engages with a bracket arranged on the rear end of the slider. Thereby the movement of the magazine expelling element is prevented as long as the filler expelling element, by releasing the finger pressure on the slider, is withdrawn under the action of its spring. The withdrawal of the magazine expelling element for a new filling of the magazine which is formed here as a tilting magazine and not an exchange magazine, is performed via a slider extending through the housing with a return pulling applied by a spring against the magazine expelling element. In this dental appliance the movements and the movements sequence of the magazine expelling element, on the one hand, and the filler expelling element, on the other hand, are neither coupled with one another, nor coordinated with one another. Both movements are performed completely independently from one another and the magazine expelling element is arranged under the action of the force applied by one spring, while the filler expelling element is arranged under the action of the force of the expelling button. In the moment of displacement of the filler expelling element, the bracket serves for lifting the action of the spring force which acts upon the magazine expelling element.

The spring which acts upon the magazine expelling element reduces its tension with emptying the magazine. Thereby the amalgam portions which are pressed by the magazine expelling element into the filler pipe are respectively degressively declined. The pre-tensioning of this magazine expelling element must be relatively high, whereby the slider because of the bracket connection between the filler expelling element and the magazine expelling element, must be displaced against a relatively high force of two pre-tensioned springs. Moreover, it is disadvantageous that for filling of the not removed magazine the dentist must return the dental appliance to its idling for filling and then either work with a second dental appliance or wait for the filling of the first dental appliance. This complicated and time consuming operational mode is especially questionable when within the frame of long-time treatment during filling of several teeth, a settling of repeated dry placements of the working field are required.

Finally, this dental appliance does not take into consideration the properties of many filler materials which are used presently in form of a silver amalgam, as these materials approximately in 5–7 minutes after mixing lose their plasticity, and the filling process must be finished within this short time period. Then, a hardening time of several hours follows. This means that the amalgam in question must be brought during a plasticizing time of approximately 5 minutes into the respective filling appliance, discharged from the filling appliance into the tooth cavity, then distributed and condensed in it.

Since in the tilting magazine of the U.S. Pat. No. 3,792,530 after the displacement of the rearwardly engaging piston of the magazine expelling element a hardened amalgam-embossement is located, withdrawal of both axes similarly to the respectively formed front end of the filler expelling element must be performed positively on hindrance.

Finally, U.S. Pat. No. 3,221,409 discloses a dental appliance of a different type. Here, a flat spring which engages a toothed rack of a filler expelling element displaces, by means of relatively high pulling knee lever, a filler expelling element in a housing formed in accordance with the principle of an injection device. Thereby, amalgam is pressed from a filler pipe which is coupled at the front end of the injection device and is replaceable. This appliance is suitable for discharge of amalgam, but not in individual small amalgam portions discharged for condensation, since within the front end of the filler expelling element and the condensing amalgam there is always a further not discharged amalgam in the filler pipe. Since, moreover, pressing forces are always applied via the entire amalgam column between the front end of the filler pipe and the discharge opening of the filler pipe, a precondensation takes place and because of the produced discharge of mercury a fast hardening takes place. This is connected with a direct prehardening and a respective depositing of the amalgam in the filler pipe.

SUMMARY OF THE INVENTION

Accordingly, it is an object of the present invention to provide a dental appliance which avoids the disadvantages of the prior art.

More particularly, it is an object of the present invention to provide a dental appliance which guarantees ergonomically favorable handling and simple mechanic construction, and at the same time can be operated by a finger, and by which small, each time separate and uniformly condensed portions can be discharged in the magazine thus avoiding a hardening.

In keeping with these objects and with others which will become apparent hereinafter, one feature of the present invention resides, briefly stated, in that a mechanical transmission includes an expelling lever which is turnably connected with a housing and which with its free end engages in the toothed rack and displaces the same during a working stroke via a finger-operated expelling button connected with the filler expelling element and also a projection in direction toward the filler pipe, before the front end of the filler expelling element which is the upper edge of the opening of the magazine in the filler pipe.

With this construction, on the one hand, the displacement of the filler expelling element and the magazine expelling element released simultaneously by the finger-actuated expelling button is coordinated by the lever turnably arranged in the housing so that the magazine expelling element presses the desirable small amalgam portion which is not subjected to pre-hardening by pressure forces, to a time point in the filler pipe when the filler expelling element has started its working stroke, but not reached the upper edge of the opening of the magazine into the filler pipe and thereby does not prevent the discharge of the small amalgam portion into the filler pipe.

Advantageously, the lever displaces the magazine expelling element during a working stroke of the filler expelling element by a path which corresponds to the diameter of the filler pipe and which simultaneously is equal to one or an integral plurality of the tooth pitch of the toothed rack.

In accordance with a first especially advantageous embodiment of the invention, the lever includes a lever crank having a rod lever with a free end engaging the toothed rack and having a crank lever turnably connected with the housing. The projection of the filler expelling element engages the crank lever and/or the rod lever in the vicinity of a hinge which connects both levers. Basically, the projection which is actuatable by the filler expelling element and extends from it, can simultaneously engage the articulately connected end of the rod lever, or the end of the crank lever, or both ends.

For displacing during each stroke of the expelling button simultaneously also the magazine expelling element by desired predetermined stroke and thereby automatically discharging the respective amalgam portion from the magazine, the rod lever is arranged under the action of a return spring. During reducing or lifting of the action of the projection of the filler expelling element, the return spring withdraws the rod lever by at least one tooth pitch in direction of the crank lever and its free end again engages into a tooth gap of the toothed rack. Since the return spring during displacing of the filler expelling element must have a tension which is sufficient for return pulling and new engaging of the lightly formed rod lever, the displacing movement of the expelling button is not affected in any significant way by this spring, in contrast to the above described solutions in the prior art.

In accordance with a second advantageous embodiment, the expelling lever includes a flat spring which is immovably mounted with its one end on the housing and engages with its free end in the toothed rack. Under the action of the projection of the filler expelling element it displaces the toothed rack, and after reducing or lifting the action of the projection springs back with its free end under the action of its own tensioning by at least one tooth pitch. This embodiment provides for an especially simple construction with a flat spring which is clamped at its one side in the housing, whereby the above described three-part lever is converted into a one-part element.

For exchanging the magazine to a new, filled magazine in a very fast manner in both embodiments, each expelling lever has an arresting projection which engages through a substantially Z-shaped opening in the housing and is disengageable from the teeth of the toothed rack via the lever when the filler expelling element is withdrawn. Thereby the magazine expelling element is uncoupled in each position of the expelling lever and can be moved back.

Because of its simple above-described construction, the new dental appliance, especially actuatable by a vibrator, considerably increases the quality of the condensation because of uniform vibration impacts of each individual discharged amalgam portion. This leads to a structure-compact and uniform amalgam condensation inside the tooth cavity. For this purpose, the front end of the filler expelling element at the end of its working stroke is displaceable via the expelling button by a small stroke to an extreme position in which the vibrator acting upon the rear end of the filler expelling element is releasable automatically.

In accordance with a further advantageous embodiment, the vibrator includes a spring motor which is driven by a manually tensionable driving spring, a cam disc which is displaceable by the spring motor in rotation, and a small hammer which is engaged by the cam disc and abuts under the action of a return spring against the end of the filler expelling element and which also is turnably movable. In the extreme position of the filler expelling element the hammer is releasable from a lock. The lock is advantageously formed of two strips on the inner edge of the drum which is provided at its end facing toward the filler expelling element with the cam disc and is also provided at its other end with the spring motor. The driving spring of the spring motor is tensionable by means of a ring which ergonomically abuts against the outer surface of the appliance and tilts the same. This tensioning is performed from the ring via a cord which automatically rolls a spring structure.

It is also possible to use a vibrator formed as an ultrasonicvibrator supplied from an electrical power source.

From U.S. Pat. No. 3,792,530 it is known to provide a vibrator which acts upon the filler expelling element. However the slider disclosed there is always connected with the filler expelling element and must move back and forth together with the latter during each working stroke. Since in this case there is a mass increase, the ergonomy and thereby the handling of the appliance is worse.

In the sense of the object of the dental appliance, its handling is considerably improved since it is formed mirror-symmetrical with two separate and differently calibrated filler and magazine expelling elements mounted on a common housing. As a result of this, the dentist is in the position to use first the small caliber working end for the small stepped regions of multi-surface tooth fillings, and by a simple turning the filling appliance by 180° as conventional for the double- and manual instruments, uses the greater caliber working end for the chewing surface region of a large area, without any time loss.

The expelling button advantageously has a surface for forward and return stroke of the filler expelling element which ergonomically matches to an indicating finger of an operator, and a ring is arranged at the side of the filler expelling element facing away of the magazine expelling element. During condensation without the vibrator the pressure of the indicating finger laid on a favorable location can be used.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 2 is a view showing a fragment II in FIG. 1;

DESCRIPTION OF THE PREFERRED EMBODIMENTS

A new dental appliance for introducing a filler material into tooth cavities is identified with reference numeral 1 and includes individual parts which are arranged in a mirror-symmetrical manner on a common housing 2. These parts include an expelling element for a filler material 3, a magazine expelling element 4, an easily exchangeable magazine 5, a finger-actuated expelling button 6, an expelling lever 7, and a vibrator 8 which acts upon an end 3′ of the filler expelling element 3. This vibration is shown in detail in FIGS. 4-7 and 10 and 11 and will be clarified in detail below.

The filler expelling element 3 is reciprocably movable in a guiding passage 9 by means of the expelling button 6. A filler pipe 10 with an exchangeable tamping end member 11 is connected with the guiding passage 9.

The magazine 5 opens with its front end 5′ into the filler pipe 10. The magazine 5 is pressed under the action of a spring 12 acting against its other end 5″, against the filler pipe 10 and during the working phase of the device is held by the spring.

A cylindrical coulisse block 13 is arranged between the magazine 5 and the spring 12 in a slidingly displaceable manner. It is provided with a respectively shaped surface at its end which faces away from the magazine 5. The magazine expelling element 4 is provided on its rear extension with a toothed rack 14. The toothed rack 14 together with the expelling lever 7 are parts of a transmission which coordinates and couples with one another the movements of the filler expelling element 3 and magazine expelling element 4, when the filler expelling element 3 performs a working stroke H which starts above an inlet opening 15 of the magazine 5 and finishes at an outlet opening 16 of the filler pipe 10.

This transmission includes in accordance with the first embodiment of the invention shown in FIGS. 4-7, a crank identified as a whole with reference numeral 17 and having a rod lever 18 which engages with its free end 19 in the toothed rack 14, and a crank lever 20 which is turnably articulately connected near a hinge 21 to the housing 2. The rod lever 18 and the crank lever 20 are connected with one another by a hinge 22. A return spring 23 engages with its one end the rod lever 18 and with its other end the housing 2 close to the hinge 21. The return spring 23 presses the rod lever 18 and/or the crank lever 20 against a projection 24 of the filler expelling element 3. The projection 24 can also be formed differently than shown in the drawings. However, in any case it must be fixedly connected with the filler expelling element 3.

Figure 4:
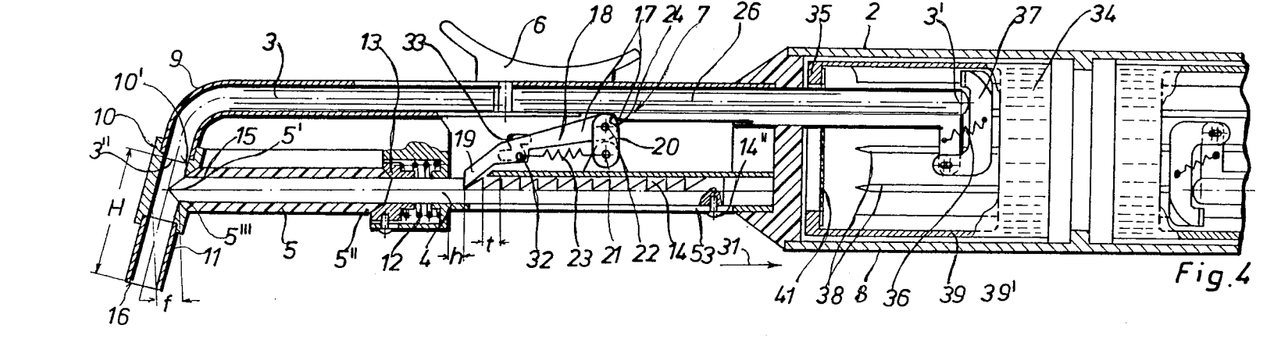
FIG. 4 is a view showing a partial longitudinal section through a left part of the dental appliance of FIG. 1 with an expelling lever formed as a crank.
Figure 5:
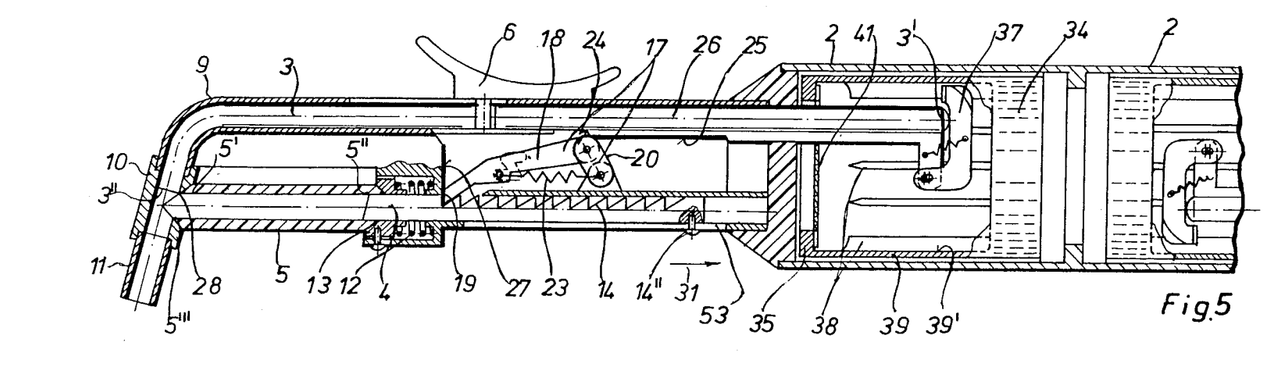
FIG. 5 is a view similar to the view of FIG. 4, in which a magazine expelling element is displaced by a tooth pitch t in direction to a filler pipe, and in this position the front end of a filler expelling element is located above the upper edge of an opening of a magazine into the filler pipe.

During displacement of the expelling button 6 from the position shown in FIG. 4 into the position shown in FIG. 5, the projection 24 in the vicinity of the hinge 22 presses against the rod lever 18 and/or the crank lever 20. Thereby the front end 19 of the rod lever 18 displaces the toothed rack 14 and therefore the magazine expelling element 4 by such a distance until the projection 24 slides over the engaging location on both above mentioned levers 18, 20. Since a strip 25 on the filler expelling element 3 is arranged at constant distance against the projection 24 from the axis of symmetry 26 of the filler expelling element 3, the expelling crank 17 during further displacement of the filler expelling element 3 remains in the position shown in FIG. 5 in which—purely accidentally—the front end 19 of the rod lever 18 travels against an abutment 27 of the housing 2. Thereby, the magazine expelling element 4 covers a working stroke h which in this case corresponds approximately to the path f in the filler pipe 10 and approximately equal to a tooth pitch t. In this manner the amalgam located in the magazine 5 during its discharge from the end 5' of the magazine 5 is not pre-condensed, but instead is cut by the returning filler expelling element 3 from the remaining amalgam column located in the magazine 5. This cutting process starts in the working phase of FIG. 5 in the vicinity of an upper edge 10' of the filler pipe 10 and ends approximately the vicinity of the upper edge 5''' of the magazine 5.

Figure 6:
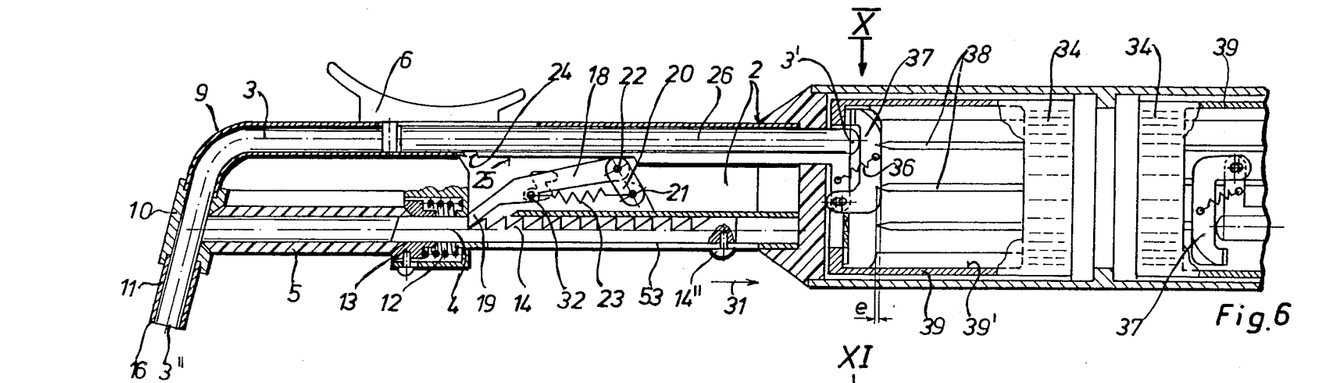
FIG. 6 is a view showing a section similar to the views of FIGS. 4 and 5, in which the magazine expelling element is located in the same position as in FIG. 5, but the filler expelling element is displaced with its free end to the outlet opening of the filler pipe.

During further displacement of the filler expelling element 3 from its position shown in FIG. 5 to its position shown in FIG. 6, the amalgam portion cut off in the filler pipe 10 is displaced from the exchangeable tamping end 11 into the tooth cavity and can be condensed there.

When the filler expelling element 3 is further displaced by the expelling button 6 from its position shown in FIG. 6 to its extreme position shown in FIG. 7 by a small stroke e, the vibrator 8 which acts upon the end 3' of the filler expelling element 3 is released, as will be explained hereinbelow.

Figure 7:
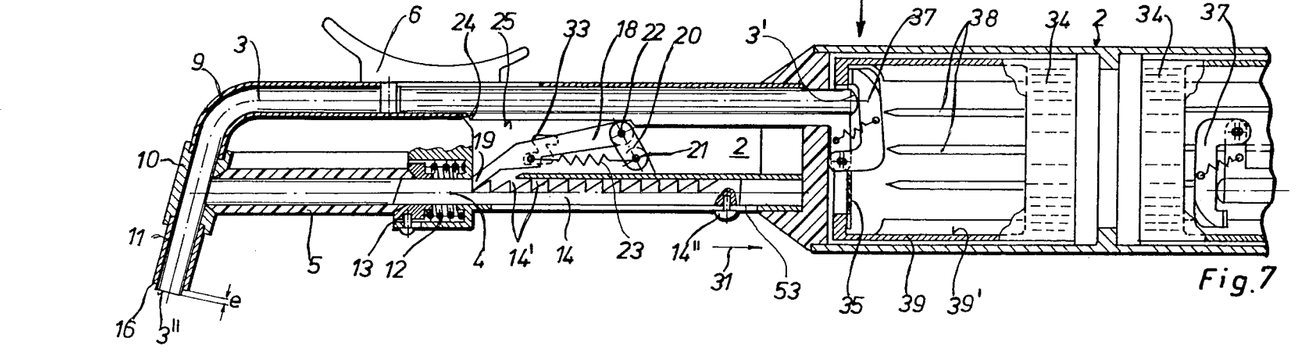
FIG. 7 is a view showing a section corresponding to the sections of FIGS. 4-6 in which the magazine expelling element assumes the same position as in FIGS. 5 and 6 but the filler expelling element is in its extreme position and displaced out of the outlet opening of the filler pipe, and then a mechanical vibrator is automatically actuated.

As can be seen from FIGS. 5-7, the crank 17 does not change its position in these three working phases. As a result of this, also the magazine expelling element 4 remains in its unchanged position, since the crank 17 is held down by the strip 25 and thereby prevented from a return movement. First when the expelling button 6 is withdrawn from its position shown in FIGS. 5-7 at least to its position shown in FIG. 4, and the action of the projection 24 and the connected strip 25 is reduced or lifted, the tension spring 23 withdraws the rod lever 18 to its position shown in FIG. 4. Thereby it is pulled back at least by a tooth pitch t in direction of the crank lever 20 and its free end 19 again engages into a following tooth gap 14' of the toothed rack 14.

Now the expelling button 6 can again be displaced forwardly in accordance with the above described phase sequence of FIGS. 5, 6 and 7. Thereby the magazine expelling element 4 again displaces a further amalgam portion into the filler pipe 10, cut off in it, and transported by the filler expelling element over its further path into the tooth cavity, and in the extreme position of FIG. 7, compressed by means of the vibrator 8 which will be described hereinbelow.

Figure 8:
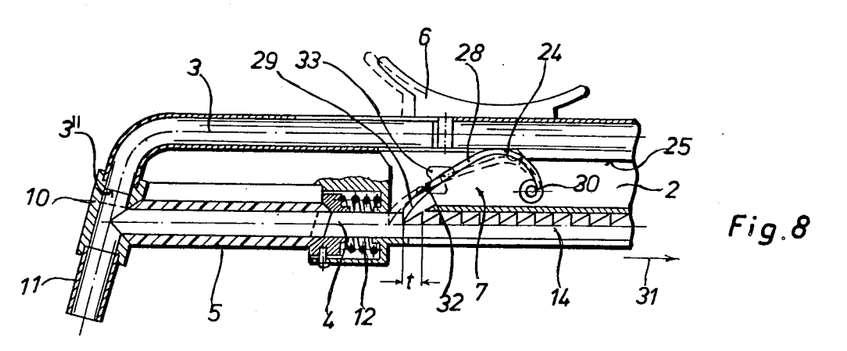
FIG. 8 is a partial section through the left half of FIG. 1 with an expelling lever which is formed as a flat spring.

A further embodiment of the expelling lever 7 is shown in FIG. 8. In this embodiment the lever 7 includes a flat spring 28 which is immovably connected by its end 30 to the housing 2, while its free end 29 engages in the toothed rack 14. Under the action of the projection 24 of the filler expelling element 3, it displaces the toothed rack 14 and after reducing or lifting the action of the projection 24 (as described with respect to FIGS. 5-7) springs back under the action of its own tension by at least one tooth pitch t to its initial position. The initial position is shown in FIG. 8 with solid lines, while the position which is changed under the action of the projection 24 and the connected strip 25 and set under a pre-tensioning is shown in broken lines.

For retracting the toothed rack 14 for exchanging the magazine 5 in direction of the arrow 31, the rod lever 18, in the embodiment of FIGS. 4-7 and the flat spring 28 in the embodiment of FIG. 8 must be pressed out from the toothed rack 14. This is achieved by an arresting projection 32 provided both in the rod lever 18 and in the flat spring 28. The arresting projection 32 engages through a substantially Z-shaped opening of the housing 2 and is disengageable from the teeth of the toothed rack 14 via the rod lever 18 by a finger, on the one hand, and the flat spring 28, on the other hand.

This disengaging possibility must be provided each time, in order to prevent that during premature retraction of the expelling button 6 before cutting off of the amalgam portion, a repeated amalgam displacement of the magazine expelling member 4 takes place. After this the magazine 5 is displaced against the force of the spring 12 in direction of the arrow 31, and the front end 5' is disengaged downwardly from the filler pipe 10, and thereby the rear end 5'' can be withdrawn from the cylindrical coulisse block 13. After this, the new filled magazine 5 is inserted in a reversed order and thereby either the rod lever 18 or the flat spring 28 can be brought by means of the arresting projection 32 again in engagement with the teeth of the toothed rack 14.

Figure 10:
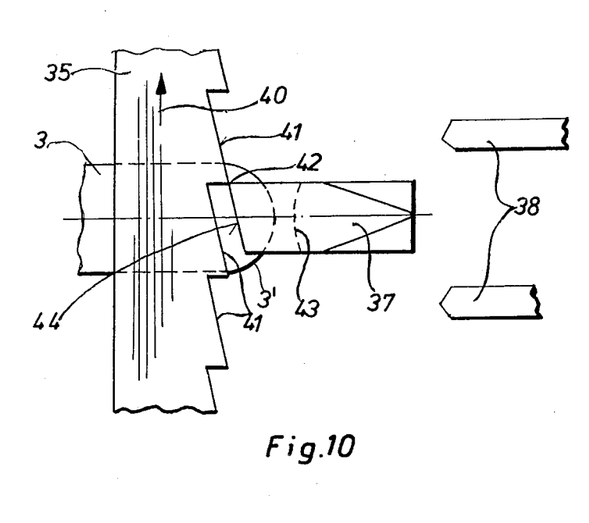
FIG. 10 is a partial plan view in direction of the arrow X in FIG. 6 of a hammer which is moved by a cam, with a part of a cam disc as well as two toothed strips of a drum acting as a lock and rotating in direction identified by the arrow.
Figure 11:
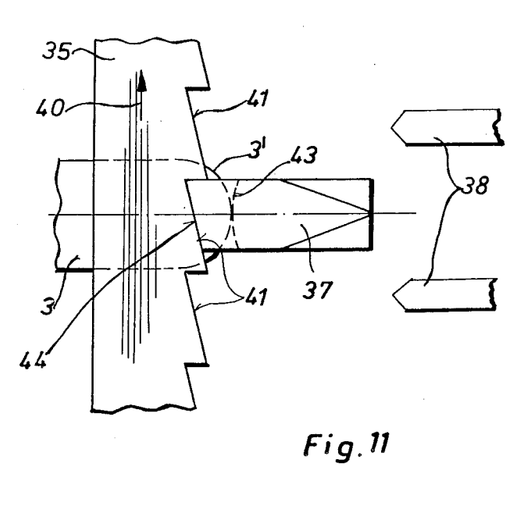
FIG. 11 is a plan view in direction XI of FIG. 7 with the hammer acting against the rear end of the filler expelling element.

The vibrator which is used in the embodiment of FIGS. 4-7 and shown in detail in FIGS. 10 and 11 includes a spring motor 34 which is driveable by a drive spring. The latter is not shown and is extendable by hand. The vibrator also includes a cam disc 35 which is driven in rotation by the spring motor 34, and a small hammer 37 which engages with the cam disc 35 and abuts against the end 3' of the filler expelling element 3 under the action of a return spring 36, and is also pivotably connected with the end 3'. In FIGS. 4-6, the hammer 37 is prevented from acting upon the end 3' of the filler expelling element 3 by a lock. This lock includes two strips 38 on an inner surface 39' of a drum 39 which is provided with the cam disc 35 at its end facing away of the filler expelling element 3 and is also provided with the spring motor 34 at its opposite end.

When in accordance with FIG. 7 the filler expelling element 3 is displaced further to its extreme position by a small path e, the hammer 37 returns between two toothed strips 38, whereby the drum 39 under the driving action of the not shown driving spring is driven in rotation. Because of this rotation, the drum 39 also rotates the cam disc 35 which is mounted thereon and with which the hammer 37 is in engagement. This process can be clearly seen from the consideration of FIGS. 10 and 11. The hammer 37 which is always pulled to the end 3' of the filler expelling element 3 by the return spring 36, slides during a rotation of the cam disc 35 in direction of the arrow 40 on a cam surface 41 to a position shown in FIG. 10 in which it is lifted from the end 3' of the filler expellling element 3, so that in the next moment shown in FIG. 11 it strikes under the action of the return spring 36 during passing the culmination point 42 against the end 3' of the filler expelling element 3. The latter transfers this impulse as a rigid body to its tip 3''.

After this this process is repeated with the following cam surface 41, whereby because of the impulse which follows in short time at the tip 3'' of the filler expelling element 3, vibrations are delivered against the filler material discharged into the tooth cavity.

In FIGS. 10 and 11, the own hammer surface which because of the view in the drawing is shown only in broken lines is identified with reference numeral 43, while the cam surface of the hammer 37 which is in engagement with the cam disc 35 and the individual cam surfaces 41 is identified with reference numeral 44.

Figure 1:
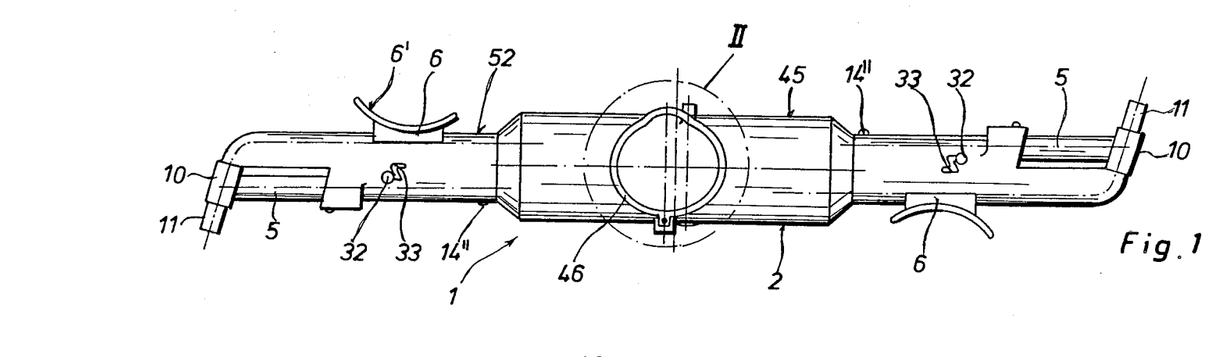
FIG. 1 is a side view of a dental appliance in accordance with the present invention.
Figure 2:
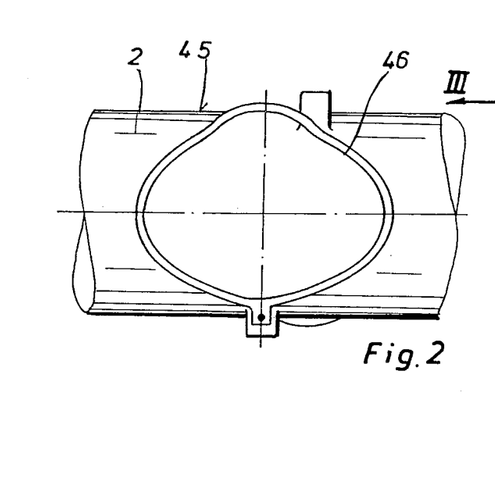
Figure 3:
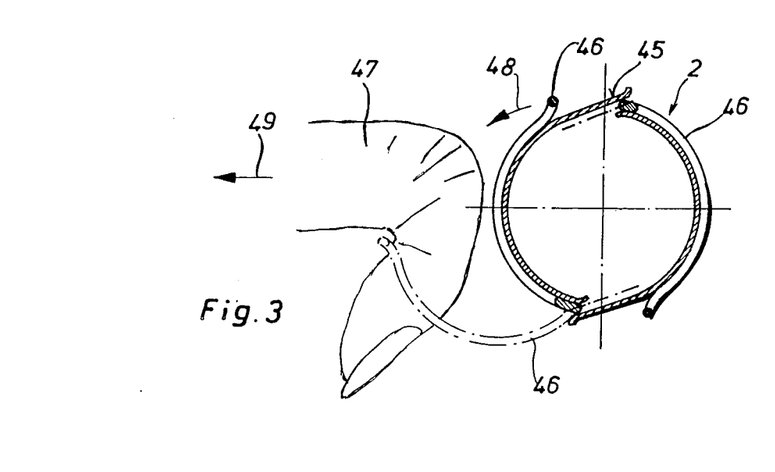
FIG. 3 is a view showing manipulation with a tiltable ring for pulling a driving spring of a spring motor in direction of the arrow III in FIG. 2.

The spring motor 34 is basically extensible by hand. This is performed in accordance with FIGS. 2 and 3 in that the driving spring can be tilted by hands in direction of the arrow 48 by means of a finger 47 over a ring 46 which ergonomically abuts against an outer surface 45 of the housing 2 and is tiltable from it. Then the ring 46 is pulled in direction of the arrow 49. After this the spring pulling automatically rolls in and the ring 46 can be tilted again against the direction of the arrow 48 to the outer surface 45 of the housing 2.

This embodiment has a special advantage in that it is completely independent from any outer energy source and thereby this tamping device is suitable for tooth treatment at locations wherein no connecting possibilities to an energy source exist.

Figure 9:
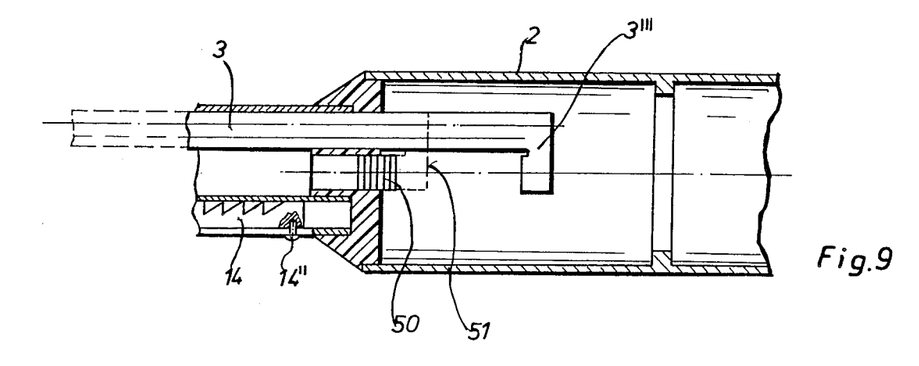
FIG. 9 is a partial section through the left half of the housing of FIG. 1, with an ultrasonic vibrator acting upon the filler expelling element.

FIG. 9 shows a further embodiment of a vibrator. In this case the vibrator is an ultrasonic vibrator 50 which always is automatically released when the end 3''' of the filler expelling element 3 which in this case is hook-shaped, is displaced to the extreme position of the tip 3'' against a resonator surface 51 of the vibrator 50 shown in broken lines. In this case coupling per finger pressure is performed via a finger of the dentist engaging the expelling bottom 6.

For guaranteeing unobjectionable handling of the expelling button 6 in both directions, it is provided with a surface 6' which ergonomically matches to the indicating finger of an operator and it is arranged at a side 52 of the filler expelling element 3 which faces away of the magazine expelling element 4.

For conveniently withdrawing the toothed rack 14 and with it the magazine expelling element 4, the toothed rack 14 is provided at its rear end with a similarly ergonomically favorably designed button which extends by means of a pin 14'' through an elongated slot 53 in the housing 2 and is releasably connected with the toothed rack 14.

For completely cleaning the appliance 1 and using the same in always hygienically unobjectibnable condition, it is made advantageously completely of metal and/or suitable high temperature-resistant synthetic plastic material, for permitting sterilization in an autoclave. It is to be understood that the new appliance can also be used without a vibrator 8. In this case, for example, the disconnected housing 2 with the spring motor 34 or the ultrasonic vibrator 50 is exchanged for an idle housing. Thereby the ergonometric length and the respective dimensions of the appliance 1 can be maintained.

It will be understood that each of the elements described above, or two or more together, may also find a useful application in other types of constructions differing from the types described above.

While the invention has been illustrated and described as embodied in a dental appliance for introducing a filler material into a tooth cavity, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A dental appliance for introducing a filler material into a cavity, comprising a support; a filler pipe; means forming a first passage; a filler expelling element reciprocatingly movable in said first passage, said filler expelling element merging into said filler pipe and having a front end; a removable magazine which accommodates a filler a plurality of portions of which can be expelled therefrom, said magazine extending transversely to said filler pipe and opening into the latter, said magazine having an inlet opening which opens into said filler pipe and is provided with an upper edge; a second passage; a magazine expelling element guided in said second passage for pressing a portion of the filler from said magazine into said filler pipe, said filler expelling element and said magazine expelling element being surrounded by said support; and mechanical transmission means which couple said filler expelling element and said magazine expelling element with one another to provide coordination of their movements, said transmission means including a toothed rack which is connected with said magazine expelling element, an expelling lever which is turnably connected with said support and having a free end engaging in said toothed rack, an expelling button which is actuatable by a finger and connected with said filler expelling element, and a projection, said lever being arranged so that during the working stroke it displaces with said toothed rack via said expelling button and said projection in direction toward said filler pipe before said front end of said filler expelling element reaches said upper end of said opening of said magazine into said filler pipe, said lever including a lever crank with a rod lever having a free end engageable in said toothed rack and with a crank lever which is turnably connected with said support, and a hinge connecting said rod lever and said crank lever with one another, said rod lever and said crank lever forming two lever members, said filler expelling element having a further projection which in the vicinity of said hinge engages at least one of said lever members.

2. A dental appliance as defined in claim 1, wherein said filler pipe has a predetermined diameter, said toothed rack having a predetermined tooth pitch, said lever being formed so that during a working stroke of said filler expelling element it displaces said magazine expelling element by a path which corresponds to the diameter of said filling pipe and also is aprpoximately equal to one tooth pitch of said toothed rack.

3. A dental appliance as defined in claim 1, wherein said toothed rack has a predetermined tooth pitch and a plurality of tooth gaps; and further comprising a return spring which acts upon said rod lever so that after reducing or removing the action of said first mentioned projection said return spring retracts said filler expelling element by at least one tooth pitch in direction of said crank lever and said free end of said rod lever again engages into one of said tooth gaps of said toothed rack.

4. A dental appliance as defined in claim 1, wherein said support has a substantially Z-shaped opening, said toothed rack having a plurality of teeth, said lever including an arresting projection which engages through said Z-shaped opening of said support and via said lever with said withdrawn filler expelling element disengages from said teeth of said toothed rack.

5. A dental appliance as defined in claim 1, wherein said filler expelling element has a rear end; and further comprising a vibrator acting upon said rear end of said filler expelling element, said front end of said filler expelling element at the end of its working stroke being further displaceable over said expelling button by a small path to an extreme position in which it automatically releases said vibrator.

6. A dental appliance as defined in claim 5; and further comprising a return spring and a lock, said vibrator including a spring motor with a manually extensible drive spring, a cam disc which is driveable in rotation by said spring motor, and a small hammer which engages with said cam disc and abuts under the action of said return spring against said rear end of said filler expelling element, said hammer being formed so that in said extreme position of said filler expelling element it is withdrawable from said lock.

7. A dental appliance as defined in claim 6, wherein said lock includes a drum having an inner surface and a tooth strip on said inner surface, said drum having an end which faces toward said filler expelling element and has said cam disc, and another end which is provided with said spring motor.

8. A dental appliance as defined in claim 6, wherein said support has an outer surface; and further comprising a ring which abuts ergonomically on said outer surface of said housing and is tiltable therefrom; an automatically rollable-up spring-biased cord, said driving spring of said spring motor being tensionable by means of said ring via said cord.

9. A dental appliance as defined in claim 6, wherein said filler expelling element has a curved end which is hook-shaped, said vibrator having a vibrator surface and being formed as an ultrasound vibrator which is supplyable from an electric current source, said vibrator being formed so that by contact of said hook-shaped end of said filler expelling element on said vibrator surface, it is releasable.

10. A dental appliance as defined in claim 1; and further comprising second such filler expelling element and second such magazine expelling element, said filler expelling elements and said magazine expelling elements being formed as two separate from one another and differently calibrated mirror-symmetrical elements which are arranged on said support.

11. A dental appliance as defined in claim 1, wherein said filler expelling element has a side which faces away of said magazine expelling element, said expelling button being provided with a surface which ergonomically corresponds to an indicating finger of an operator for reciprocation of said filler expelling element, said expelling button being arranged at said side of said filler expelling element which faces away of said magazine expelling element.

12. A dental appliance as defined in claim 1, wherein all parts of the dental appliance are composed of metal, and are jointly sterilizable in an autoclave.

13. A dental appliance as defined in claim 1, wherein all parts of the dental appliance are composed of tetrafluoroethylene and are jointly sterilizable in an autoclave.

14. A dental appliance as defined in claim 1, wherein said filler pipe has a predetermined diameter, said toothed rack having a predetermined tooth pitch, said lever being formed so that during a working stroke of said filler expelling element it displaces said magazine expelling element by a path which corresponds to the diameter of said filling pipe and also is approximately equal to an integral plurality of the tooth pitch of said toothed rack.

15. A dental appliance for introducing a filler material into a cavity, comprising a support; a filler pipe; means forming a first passage; a filler expelling element reciprocating movable in said first passage, said filler expelling element merging into said filler pipe and having a front end; a removable magazine which accomodates a filler a plurality of portions of which can be expelled therefrom, said magazine extending transversely to said filler pipe and opening into the latter, said magazine having an inlet opening which opens into said filler pipe and is provided with an upper edge; a second passage; a magazine expelling element guided in said second passage for pressing a portion of the filler from said magazine into said filler pipe, said filler expelling element and said magazine expelling element being surrounded by said support; and mechanical transmission means which couple said filler expelling element and said magazine expelling element with one another to provide corrdination of their movements, said transmission means including a toothed rack which is connected with said magazine expelling element, an expelling lever which is turnably connected with said support and having a free end engaging in said toothed rack, an expelling button which is actuatable by a finger and connected with said filler expelling element, and a projection, said lever being arranged so that during the working stroke it displaces with said toothed rack via said expelling button and said projection in direction toward said filler pipe before said front end of said filler expelling element reaches said upper end of said opening of said magazine into said filler pipe, wherein said toothed rack has a predetermined tooth pitch, said lever including a flat spring which has one end immovably connected with said support and a free end engaging into said toothed rack, said flat spring displacing said toothed rack under the action of said first mentioned projection of said filler expelling element, and after reducing or removing the action of said first mentioned projection with its free end springsback under the action of its own tensioning by at least one tooth pitch to its initial position.

16. A dental appliance for introducing a filler material into a cavity, comprising a support; a filler pipe; means forming a first passage; a filler expelling element reciprocatingly movable in said first passage, said filler expelling element merging into said filler pipe and having a front end; a removable magazine which accommodates a filler, a plurality of portions of which can be expelled therefrom, said magazine extending transversely to said filler pipe and opening into the latter, said magazine having an inlet opening which opens into said filler pipe and is provided with an upper edge; a second passage; a magazine expelling element guided in said second passage for pressing a portion of the filler from said magazine into said filler pipe, said filler expelling element and said magazine expelling element being surrounded by said support; and mechanical transmission means which couple said filler expelling element and said magazine expelling element with one another to provide coordination of their movement, said transmission means including a toothed rack which is connected with said magazine expelling element, an expelling lever which is turnably connected with said support and having a free end engaging in said toothed rack, an expelling button which is actuatable by a finger and connected with said filler expelling element, and a projection, said lever being arranged so that during the working stroke it displaces with said toothed rack via said expelling button and said projection in direction toward said filler pipe before said front end of said filler expelling element reaches said upper end of said opening of said magazine into said filler pipe, said support having a substantially Z-shaped opening, said toothed rack having a plurality of teeth, said lever including an arresting projection, which engages in said Z-shapecd opening of said support, and via said lever with said withdrawn filler expelling element disengages from said teeth of said toothed rack.

* * * * *